(12) United States Patent
Castaldi et al.

(10) Patent No.: US 7,385,062 B2
(45) Date of Patent: Jun. 10, 2008

(54) PROCESS FOR THE PREPARATION OF PHENYLTETRAZOLE DERIVATIVES

(75) Inventors: Graziano Castaldi, Briona (IT); Pietro Allegrini, San Donato Milanese (IT); Gabriele Razzetti, Sesto S. Giovanni (IT); Alberto Bologna, Crema (IT); Marcello Rasparini, Pieve Ligure (IT); Vittorio Lucchini, San Donato Milanese (IT)

(73) Assignee: Dipharma S.p.A., Mereto Di Tomba (IT)

( * ) Notice: Subject to any disclaimer, the term of this patent is extended or adjusted under 35 U.S.C. 154(b) by 87 days.

(21) Appl. No.: 10/567,492

(22) PCT Filed: Jul. 30, 2004

(86) PCT No.: PCT/EP2004/008576

§ 371 (c)(1),
(2), (4) Date: Feb. 7, 2006

(87) PCT Pub. No.: WO2005/014560

PCT Pub. Date: Feb. 17, 2005

(65) Prior Publication Data

US 2006/0183916 A1    Aug. 17, 2006

(30) Foreign Application Priority Data

Aug. 8, 2003  (IT)  .......................... MI2003A1638
May 7, 2004   (IT)  .......................... MI2004A0929

(51) Int. Cl.
*C07D 257/04*  (2006.01)

(52) U.S. Cl. ..................................... 548/252; 548/250
(58) Field of Classification Search ............... 548/250, 548/252

See application file for complete search history.

(56) References Cited

U.S. PATENT DOCUMENTS 6,271,375 B1 *  8/2001  Villa et al. ................. 544/279

FOREIGN PATENT DOCUMENTS

| EP | 0 418 013   | 3/1991 |
| WO | WO 93/10106 | 5/1993 |
| WO | WO 99/01459 | 1/1999 |

* cited by examiner

*Primary Examiner*—Golam M. M. Shameem
(74) *Attorney, Agent, or Firm*—Young & Thompson

(57) ABSTRACT

A process for the preparation of phenyltetrazole derivatives of formula (II) wherein R and Y are as defined in the disclosure, by direct ortho-metallation of (tetrazol-5-yl)benzene. The compounds of formula (II) are useful intermediates for the preparation of angiotensin II antagonists.

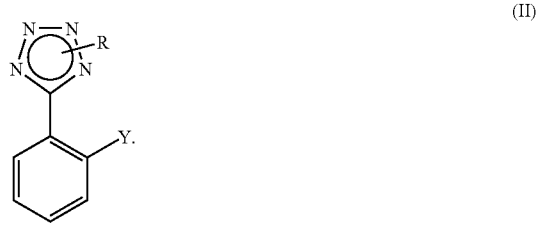

8 Claims, No Drawings

PROCESS FOR THE PREPARATION OF PHENYLTETRAZOLE DERIVATIVES

FIELD OF THE INVENTION

The present invention relates to a process for the preparation of substituted phenyltetrazole compounds, useful as intermediates for the preparation of angiotensin II antagonists.

BACKGROUND OF THE INVENTION

Angiotensin II antagonists are used, for example, in the treatment of hypertension, anxiety, glaucoma and heart failure. A number of these compounds are characterized by a biphenyltetrazole moiety and can be represented by the following formula (I)

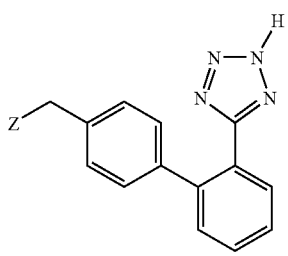

(I)

wherein Z is an optionally substituted heterocycle containing at least one nitrogen atom; or an amido residue.

Preferably, the residue Z has the following meanings, which identify specific angiotensin II antagonists:

2-butyl-4-chloro-5-hydroxymethyl-imidazol-1-yl (losartan);

2-ethoxy-7-carboxy-1H-benzimidazol-1-yl (candesartan);

2-butyl-1,3-diaza-spiro[4,4]non-1-en-4-on-3-yl (irbesartan); and (S)—N-(1-carboxy-2-methylprop-1-yl)-N-pentanoylamino (valsartan).

Key intermediates for the preparation of compounds of formula (I) are 2-substituted phenyltetrazoles of formula (II)

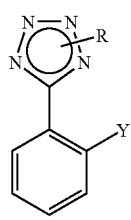

(II)

in which R is hydrogen, a protecting group or a salifying group and Y is a —B(OR$_4$)$_2$ group, wherein each R$_4$ is independently hydrogen or C$_1$-C$_6$ alkyl; or a ZnX group, wherein X is a halogen atom selected from chlorine, bromine and iodine.

A number of processes for the preparation of the compounds of formula (II) are known. For example, the process disclosed in U.S. Pat. No. 5,039,814 or in WO 93/10106 comprises the ortho-litiation of the phenyltetrazole and the subsequent transmetallation reaction. The main drawbacks of said process resides in the need to use an organo-lithium compound, i.e. a compound which requires specific safety precautions when used on an industrial scale, due to its high flammability and reactivity.

WO 99/01459 partly solves the problems deriving from the use of organo-lithium compounds by reacting a compound of formula (III)

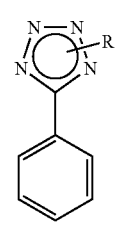

(III)

in which R is as defined above,
with a Grignard reagent of formula

R$_1$—MgX in which R$_1$ is C$_1$-C$_6$ alkyl or benzyl and X is as defined above;

in the presence of catalytic amounts of a secondary amine, which acts as a disaggregant of the Grignard reagent;

thereby obtaining a compound of formula (IV)

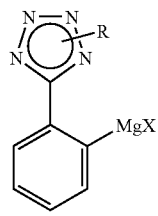

(IV)

wherein R and X are as defined above. This compound is however hardly reactive and cannot be used as such in "cross-coupling" reactions for the preparation of compounds of formula (I). Therefore, this compound is subjected to a transmetallation reaction, according to known procedures, to obtain a compound of formula (II) as defined above, which is much more reactive. The use of a Grignard reagent, compared with an organo-lithium compound, is undoubtedly safer, but still potentially dangerous on an industrial scale and still requires specific procedures.

It is therefore evident that there is still need for an alternative process for the preparation of compounds of formula (II), in particular a process which does not require the use of Grignard reagents.

DETAILED DESCRIPTION OF THE INVENTION

It has now been found a process for the preparation of compounds of formula (II) which does not involve the use of Grignard reagents and is therefore safer; furthermore, this process is more advantageous from the industrial point of view as it provides higher yields, is less costly and involves less preparation steps.

Therefore, the present invention relates to a process for the preparation of compounds of formula (II)

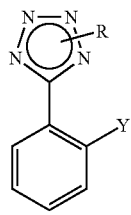

(II)

wherein R is hydrogen, a protecting group or a salifying group and Y is a —B(OR$_4$)$_2$ group, in which each R$_4$ is independently hydrogen or C$_1$-C$_6$ alkyl; or a —ZnX group, wherein X is a halogen atom selected from chlorine, bromine and iodine;

which comprises the reaction of a compound of formula (V)

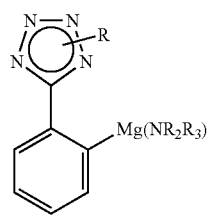

(V)

wherein R is as defined above and R$_2$ and R$_3$, which can be the same or different, are straight or branched C$_1$-C$_6$ alkyl, C$_3$-C$_6$ cycloalkyl, trialkylsilyl, or R$_2$ and R$_3$, taken together with the nitrogen atom they are linked to, form a saturated, optionally substituted, heterocyclic ring, containing one to two further heteroatoms independently selected from nitrogen, oxygen and sulfur;

either with a compound of formula (VI)

ZnX$_2$ (VI)

wherein X is as defined above;

or with a compound of formula (VIa)

B(OR'$_4$)$_3$ (VIa)

wherein each R'$_4$ is independently C$_1$-C$_6$ alkyl, and, if desired, the subsequent hydrolysis of the resulting boronic ester of formula (II).

The term "protecting group R" means a tetrazole ring protecting group known in the art, preferably a straight or branched C$_1$-C$_6$ alkyl, optionally substituted with one or more phenyl groups, in their turn optionally substituted, for example with C$_1$-C$_4$ alkoxy or C$_1$-C$_4$ alkylthio. Preferred examples of R are tert-butyl, para-methoxybenzyl, trityl and 1-methyl-1-phenylethyl, the latter being particularly preferred.

The term "salifying group R" means, for example, an alkali or alkaline-earth metal, preferably sodium, potassium or magnesium, more preferably sodium.

When R$_2$ and R$_3$ are C$_1$-C$_6$ alkyl groups, they are preferably C$_3$-C$_6$ alkyl groups, more preferably isopropyl, sec-butyl, tert-butyl, most preferably isopropyl.

When R$_2$ and R$_3$ are C$_3$-C$_6$ cycloalkyl groups, they are preferably cyclopentyl and cyclohexyl.

When R$_2$ and R$_3$ are trialkylsilyl groups, they are preferably trimethylsilyl.

When R$_4$ is a C$_1$-C$_6$ alkyl group, it is preferably a straight or branched C$_1$-C$_4$ alkyl group, more preferably methyl, ethyl propyl, isopropyl, sec-butyl, tert-butyl, most preferably methyl, ethyl or isopropyl.

The term "heterocyclic ring" as defined above preferably means piperidine, piperazine, morpholine, pyrrolidine, more preferably 2,2,6,6-tetramethylpiperidine.

The reaction of a compound of formula (V) with a compound of formula (VI) or (VIa) is typically carried out in an ether solvent, preferably ethyl ether, dioxane, methyl tert-butyl ether, tetrahydrofuran or mixtures thereof, or mixtures thereof with apolar solvents, preferably hexane, heptane, cyclohexane, benzene, toluene and xylene, more preferably tetrahydrofuran. The stoichiometric ratio of a compound of formula (VI) or (VIa) to a compound of formula (V) ranges from approx. 1.0 to approx. 5.0, preferably from 1.1 to 3.0. The reaction is carried out at a temperature ranging from about 20° C. to the reflux temperature of the reaction mixture. Reaction times depend on the temperature and the progress of the reaction is monitored by conventional analytical methods.

The hydrolysis of a boronic ester of formula (II) to obtain a corresponding compound of formula (II) in which R$_4$ is hydrogen, can be carried out according to known methods, for example by addition of a mineral or organic acid, in particular phosphoric, hydrochloric or acetic acid, to the reaction mixture.

The compounds of formula (II) wherein R is a 1-methyl-1-phenyl-ethyl group and Y is a —B(OR$_4$)$_2$ group, in which R$_4$ is as defined above, are novel and are a further object of the invention.

Preferred examples are those in which each R$_4$ is independently hydrogen, methyl, ethyl or isopropyl.

Particularly preferred are the following compounds:
2-[2-(1-methyl-1-phenyl-ethyl)-2H-tetrazol-5-yl]-phenylboronic acid;
2-[2-(1-methyl-1-phenyl-ethyl)-2H-tetrazol-5-yl]-phenylboronic acid methyl ester; and
2-[2-(1-methyl-1-phenyl-ethyl)-2H-tetrazol-5-yl]-phenylboronic acid isopropyl ester.

The compounds of formula (V) are novel and are a further object of the present invention.

Preferred examples of compounds of formula (V) are:
2-[2-t-butyl-2H-tetrazol-5-yl]-phenyl magnesium diisopropylamide;
2-[2-sodium-2H-tetrazol-5-yl]-phenyl magnesium diisopropylamide; and
2-[2-(1-methyl-1-phenyl-ethyl)-2H-tetrazol-5-yl]-phenyl magnesium diisopropylamide,
in particular the latter.

Compounds (V) can be prepared by reaction of compounds of formula (III)

(III)

wherein R is as defined above,
with compounds of formula (VII)

$$Mg(NR_2R_3)_2 \quad (VII)$$

wherein $R_2$ and $R_3$ are as defined above.

The reaction between a compound of formula (III) and a compound of formula (VII) is typically carried out in an ether solvent, for example ethyl ether, dioxane, methyl tert-butyl ether, tetrahydrofuran or mixtures thereof, or mixtures thereof with apolar solvents, preferably hexane, heptane, cyclohexane, benzene, toluene and xylene, more preferably tetrahydrofuran. The stoichiometric ratio of a compound of formula (VII) to a compound of formula (III) ranges from approx. 0.5 to approx. 3.0, preferably from 1.0 to 2.0. The reaction is carried out at a temperature ranging from about 20° C. to the reflux temperature of the reaction mixture, preferably at the reflux temperature. Reaction times depend on the temperature, and the progress of the reaction is monitored by conventional analytical methods. The resulting compound of formula (V), which can optionally be isolated, is then reacted with a compound of formula (VI) or (VIa).

The compounds of formula (VII) can be obtained according to known processes, for example as described in DE 100 61 317. Preferably, the resulting compounds of formula (VII) are reacted with compounds of formula (III) without being isolated.

A further object of the invention is the use of a compound of formula (V) for the preparation of a compound of formula (I)

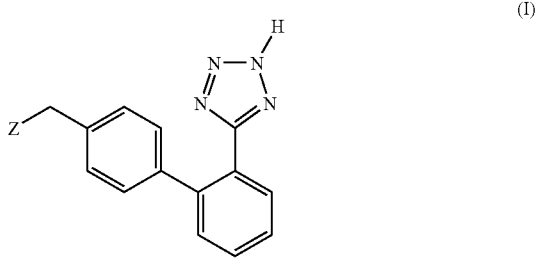

or a pharmaceutically acceptable salt thereof, in which Z is an optionally substituted heterocycle, containing at least one nitrogen atom; or an amido residue.

Preferably, a compound of formula (V) is used for the preparation of a compound of formula (I) in which Z is selected from:
2-butyl-4-chloro-5-hydroxymethyl-imidazol-1-yl;
2-ethoxy-7-carboxy-1H-benzimidazol-1-yl;
2-butyl-1,3-diaza-spiro[4,4]non-1-en-4-on-3-yl and
(S)-N-(1-carboxy-2-methylprop-1-yl)-N-pentanoylamino,
most preferably 2-butyl-4-chloro-5-hydroxymethyl-imidazol-1-yl.

The preparation of a compound of formula (I) from a compound of formula (II) can be carried out for example according to EP 846117 or WO 95/32962.

The following examples further illustrate the invention.

EXAMPLE 1

Preparation of 2-[2-(1-methyl-1-phenyl-ethyl)-2H-tetrazol-5-yl]-phenyl zinc chloride (II)

A mixture of 2-(1-methyl-1-phenyl-ethyl)-5-phenyl-2H-tetrazole (5.0 g; 20.3 mmoles) and magnesium diisopropylamide (0.75 M solution in THF; 40 ml) is refluxed for 3 hrs. The mixture is subsequently cooled and diluted with a zinc chloride solution (5.4 g; 40.0 mmoles) in THF (29 ml). The resulting mixture is refluxed for a further 2 hrs.

$^1$H-NMR analysis, after treatment with deuterated water, evidences a conversion to organo-zinc higher than 96%.

EXAMPLE 2

Preparation of 2-[2-Trityl-2H-tetrazol-5-yl]-phenyl magnesium diisopropylamide (V)

A mixture of 1-trityl-5-phenyl-2H-tetrazole (7.9 g; 20.3 mmoles) and magnesium diisopropylamide (0.75 M solution in THF; 40 ml) is refluxed for 3 hrs.

$^1$H-NMR analysis, after treatment with deuterated water, evidences a 67% conversion to organo-magnesium.

EXAMPLE 3

Preparation of 2-[2-t-butyl-2H-tetrazol-5-yl]-phenyl magnesium diisopropylamide (V)

A mixture of 1-t-butyl-5-phenyl-2H-tetrazole (4.1 g; 20.3 mmoles) and magnesium diisopropylamide (0.75 M solution in THF; 40 ml) is refluxed for 3 hrs.

$^1$H-NMR analysis, after treatment with deuterated water, evidences a 75% conversion to organo-magnesium.

EXAMPLE 4

Preparation of 2-[2-sodium-2H-tetrazol-5-yl]-phenyl magnesium diisopropylamide (V)

A mixture of 5-phenyl-2H-tetrazole sodium salt (3.4 g; 20.3 mmoles) and magnesium diisopropylamide (0.75 M solution in THF; 40 ml) is refluxed for 3 hrs.

$^1$H-NMR analysis, after treatment with deuterated water, evidences a 75% conversion to organo-magnesium.

EXAMPLE 5

Preparation of 2-(2-(1-methyl-1-phenyl-ethyl)-2H-tetrazol-5-yl)-phenyl)-magnesium isopropylamide (V)

A 2 liters reactor is loaded with 600 ml of a magnesium diisopropylamide 0.75 M solution and 100 g of 2-(1-methyl-1-phenyl-ethyl)-5-phenyl-2H-tetrazole. The mixture is refluxed for 4 hrs., then the reaction is seeded with 1 g of 2-(2-(1-methyl-1-phenyl-ethyl)-2H-tetrazol-5-yl)-phenyl)-magnesium isopropylamide and then refluxed for a further 16 hrs. The resulting mixture is cooled to 20-30° C., filtered by suction under inert atmosphere, then washed with THF to afford 102 g 2-(2-(1-methyl-1-phenyl-ethyl)-2H-tetrazol-5-yl)-phenyl)-magnesium isopropylamide.

$^1$H NMR (CD$_3$OD), (δ, ppm): 8.15 (1H, m); 7.43 (3H, m); 7.31 (3H, m); 7.18 (2H, d); 2.91 (2H, set); 2.20 (6H, s); 1.02 (12H, d).

EXAMPLE 6

Preparation of 2-(2-(1-methyl-1-phenyl-ethyl)-2H-tetrazol-5-yl)-phenyl)-boronic acid (II)

A 2 liters reactor is loaded with 102 g 2-(2-(1-methyl-1-phenyl-ethyl)-2H-tetrazol-5-yl)-phenyl)-magnesium isopropylamide and 250 ml of THF. The suspension is cooled to 0-5° C. and added with 58.3 g of trimethylborate in 20 minutes. The mixture is then gradually heated to room temperature, left under stirring for at least 2 hrs., then diluted to pH 2.5-3 with phosphoric acid. The resulting solution is heated to 30-35° C. and kept at this temperature for 2 hrs., then stirring is interrupted and the aqueous phase is discarded. 250 ml of water are added to the organic phase and the resulting mixture is concentrated under vacuum to remove THF. The resulting mixture is diluted with 60 ml of toluene and left under stirring at room temperature for at least 3 hrs. The precipitated product is filtered and washed with water and toluene. After drying a 60° C. under vacuum, 60 g of 2-(2-(1-methyl-1-phenyl-ethyl)-2H-tetrazol-5-yl)-phenyl)-boronic acid are obtained.

$^1$H NMR (DMSO d$_6$), (δ, ppm): 8.00 (2H, s); 7.90 (1H, m); 7.48 (3H, m); 7.31 (3H, m); 7.18 (2H, d); 2.15 (6H, s).

EXAMPLE 7

Preparation 2-(2-(1-methyl-1-phenyl-ethyl)-2H-tetrazol-5-yl)-phenyl)-boronic acid methyl ester (II)

A 2 liters reactor is loaded with 102 g 2-(2-(1-methyl-1-phenyl-ethyl)-2H-tetrazol-5-yl)-phenyl)-magnesium isopropylamide and 250 ml of THF. The suspension is cooled to 0-5° C. and added with 58.3 g of trimethylborate, in 20 minutes. The mixture is then gradually heated to room temperature, left under stirring for at least 2 hrs., then diluted with water and toluene. The aqueous phase is discarded and the organic phase is evaporated to a residue. 70 g of an oil consisting of 2-(2-(1-methyl-1-phenyl-ethyl)-2H-tetrazol-5-yl)-phenyl)-boronic acid methyl ester methyl ester.

$^1$H NMR (DMSO d$_6$), (δ, ppm): 7.90 (1H, m); 7.48 (3H, m); 7.31 (3H, m); 7.18 (2H, d); 3.17 (6H, s); 2.15 (6H, s).

Following the same procedure, 2-(2-(1-methyl-1-phenyl-ethyl)-2H-tetrazol-5-yl)-phenyl)-boronic acid isopropyl ester is obtained.

The invention claimed is:

1. A compound of formula (V)

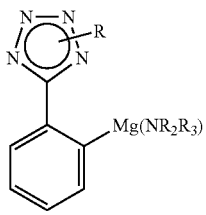

(V)

wherein,
R is selected from the group consisting of hydrogen, a protecting group, and a salifying group, and
R$_2$ and R$_3$ are one of (i) the same or different and are selected from the group consisting of a straight or a branched C$_1$-C$_6$ alkyl group, a C$_3$-C$_6$ cycloalkyl group, and a trialkylsilyl group and (ii) taken together with the nitrogen atom to which they are linked form a saturated, optionally substituted, heterocyclic ring, containing one to two further heteroatoms independently selected from the group consisting of nitrogen, oxygen and sulfur.

2. The compound according to claim 1, wherein said compound is selected from the group consisting of:
2-[2-t-butyl-2H-tetrazol-5-yl]-phenyl magnesium diisopropylamide;
2-[2-sodium-2H-tetrazol-5-yl]-phenyl magnesium diisopropylamide; and
2-[(1-methyl-1-phenyl-ethyl)-2H-tetrazol-5yl]-phenyl magnesium diisopropylamide.

3. A method of preparing a compound of formula (I) from a compound of formula (V), comprising:
reacting the compound of formula (V) with one of a compound of formula (VI) and a compound of (VIa) to form a compound of formula (II),
the compound of formula (V) being

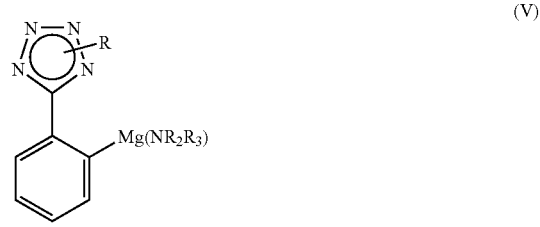

(V)

where R is selected from the group consisting of hydrogen, a protecting group, and a salifying group, and R$_2$ and R$_3$ are one of (i) the same or different and are selected from the group consisting of a straight or a branched C$_1$-C$_6$ alkyl group, a C$_3$-C$_6$ cycloalkyl group, and a trialkylsilyl group and (ii) taken together with the nitrogen atom to which they are linked form a saturated, optionally substituted, heterocyclic ring, containing one to two further heteroatoms independently selected from the group consisting of nitrogen, oxygen and sulfur,
the compound of formula (VI) being

ZnX$_2$ (VI)

where X is a halogen atom selected from the group consisting of chlorine, bromine and iodine,
the compound of formula (VIa) being

B(OR'$_4$)$_3$ (VIa)

where each R'$_4$ is independently a C$_1$-C$_6$ alkyl group, and the compound of formula (II) being

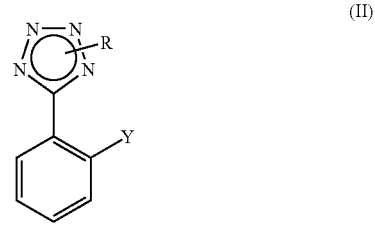

(II)

where R is selected from the group consisting of hydrogen, a protecting group and a salifying group, Y is one of (i) a —ZnX group and (ii) a —B(OR$_4$)$_2$, X is a halogen atom selected from the group consisting of chlorine, bromine and iodine, and each R'$_4$ is independently a C$_1$-C$_6$ alkyl group;

optionally hydrolyzing the resulting bornic ester of formula (II); and producing the compound of formula (I) from the compound of formula (II), the compound of formula (I) being

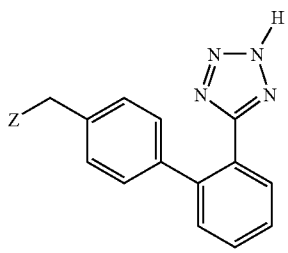
(I)

or a pharmaceutically acceptable salt thereof, where Z is one of (i) an optionally substituted heterocycle containing at least one nitrogen atom and (ii) an amido residue,

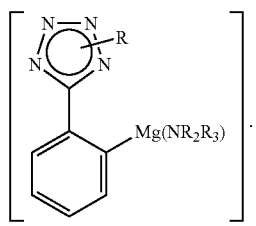
(V)

4. The method according to claim 3, wherein in the compound of formula (I) the residue Z is selected from:

2-butyl-4-chloro-5-hydroxymethyl-imidazol-1-yl;

2-ethoxy-7-carboxy-1H-benzimidazol-1-yl;

2-butyl-1,3-diaza-spiro[4,4]non-1-en-4-on-3-yl; and (S) —N-(1-carboxy-2-methylprop-1-yl)-N-pentanoylamino.

5. A method of preparing a compound of formula (I) from a compound of formula (V), comprising:

reacting the compound of formula (V) with one of a compound of formula (VI) and a compound of (VIa) to form a compound of formula (II), the compound of formula (V) being selected from the group consisting of: 2-[2-t-butyl-2H-tetrazol-5-yl]-phenyl magnesium diisopropylamide, 2-[2-sodium-2H-tetrazol-5-yl]-phenyl magnesium diisopropylamide, and 2-[2-(1-methyl-1-phenyl-ethyl)-2H-tetrazol-5-yl]-phenyl magnesium diisopropylamide, the compound of formula (VI) being ZnX₂ (VI)

where X is a halogen atom selected from the group consisting of chlorine, bromine and iodine, the compound of formula (VIa) being B(OR'₄)₃ (VIa)

where each R'₄ is independently a $C_1$-$C_6$ alkyl group, and the compound of formula (II) being

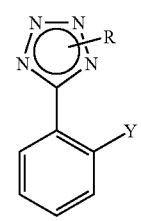
(II)

where R is selected from the group consisting of hydrogen, a protecting group and a salifying group, Y is one of (i) a —ZnX group and (ii) a —B(OR₄)₂, X is a halogen atom selected from the group consisting of chlorine, bromine and iodine, and each R'₄ is independently a $C_1$-$C_6$ alkyl group;

optionally hydrolyzing the resulting bornic ester of formula (II); and producing the compound of formula (I) from the compound of formula (II), the compound of formula (I) being

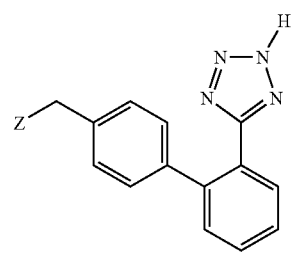
(I)

or a pharmaceutically acceptable salt thereof, where Z is one of (i) an optionally substituted heterocycle containing at least one nitrogen atom and (ii) an amido residue.

6. The method according to claim 3, wherein the reaction of formula (V) with one of a compound of formula (VI) and a compound of (VIa) is carried out at a stoichiometric ratio from 1.0 to 5.0 of the one of compound of formula (VI) and the compound of (VIa) to the compound of formula (V).

7. The method according to claim 6, wherein the stoichiometric ratio is from 1.1 to 3.0.

8. The method according to claim 3, wherein the reaction of formula (V) with one of a compound of formula (VI) and a compound of (VIa) is carried out in an ether solvent or mixtures thereof with an apolar solvent, at a temperature ranging from 20° C. to the reflux temperature.

* * * * *